United States Patent
Sgroi, Jr.

(10) Patent No.: US 10,973,142 B2
(45) Date of Patent: Apr. 6, 2021

(54) HERMETICALLY SEALED PRINTED CIRCUIT BOARDS

(71) Applicant: Covidien LP, Mansfield, MA (US)

(72) Inventor: Anthony Sgroi, Jr., Wallingford, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/812,562

(22) Filed: Mar. 9, 2020

(65) Prior Publication Data
US 2020/0214159 A1   Jul. 2, 2020

Related U.S. Application Data

(63) Continuation-in-part of application No. 16/270,721, filed on Feb. 8, 2019, now Pat. No. 10,667,408, which is a continuation-in-part of application No. 15/947,314, filed on Apr. 6, 2018, now Pat. No. 10,588,231.

(60) Provisional application No. 62/508,101, filed on May 18, 2017.

(51) Int. Cl.
| | |
|---|---|
| H05K 5/00 | (2006.01) |
| H05K 5/06 | (2006.01) |
| H05K 3/30 | (2006.01) |
| H05K 1/18 | (2006.01) |
| A61B 17/00 | (2006.01) |

(52) U.S. Cl.
CPC ............ *H05K 5/069* (2013.01); *A61B 17/00* (2013.01); *H05K 1/189* (2013.01); *H05K 3/303* (2013.01); *H05K 5/0043* (2013.01); *A61B 2017/0046* (2013.01); *H05K 2201/10151* (2013.01); *H05K 2203/166* (2013.01)

(58) Field of Classification Search
CPC .. H05K 5/0043; H05K 5/0047; H05K 5/0052; H05K 5/0056; H05K 5/006; H05K 5/0095
See application file for complete search history.

(56) References Cited

U.S. PATENT DOCUMENTS

| | | | |
|---|---|---|---|
| 4,372,037 A | 2/1983 | Scapple et al. | |
| 4,420,652 A | 12/1983 | Ikeno | |
| 4,672,418 A | 6/1987 | Moran et al. | |

(Continued)

FOREIGN PATENT DOCUMENTS

| | | |
|---|---|---|
| CN | 1313637 A | 9/2001 |
| DE | 3913066 A1 | 11/1990 |

(Continued)

OTHER PUBLICATIONS

Machine Translation of DE102013204018, Weiss, Markus, Sep. 2014 (Year: 2014).*

(Continued)

*Primary Examiner* — Jeremy C Norris

(57) ABSTRACT

A method of assembling a hermetically sealed printed circuit board includes: securing a flange of a cap against an electrical contact region on a first side of a substrate, the flange extending across a first end portion of a wall of the cap, the wall extending around the electrical contact region and including a second end portion disposed in an open configuration; and closing the second end portion of the wall to form a hermetically sealed chamber around the electrical contact region.

20 Claims, 6 Drawing Sheets

(56) References Cited

U.S. PATENT DOCUMENTS

| | | |
|---|---|---|
| 5,041,943 A | 8/1991 | Ilardi et al. |
| 5,223,741 A | 6/1993 | Bechtel et al. |
| 5,280,413 A | 1/1994 | Pai |
| 5,497,290 A | 3/1996 | Fukui et al. |
| 5,940,279 A | 8/1999 | Gademann et al. |
| 6,320,128 B1 | 11/2001 | Glovatsky et al. |
| 6,351,194 B2 | 2/2002 | Takahashi et al. |
| 6,449,168 B1 | 9/2002 | Soderholm |
| 7,659,617 B2 | 2/2010 | Kang et al. |
| 7,898,074 B2 | 3/2011 | Eckhardt et al. |
| 8,354,587 B2 | 1/2013 | Tappel et al. |
| 8,666,505 B2 | 3/2014 | O'Brien et al. |
| 8,756,801 B2 | 6/2014 | Nall |
| 9,442,131 B2 | 9/2016 | Hazel et al. |
| 10,667,408 B2 | 5/2020 | Sgroi, Jr. et al. |
| 2008/0128886 A1 | 6/2008 | Kang et al. |
| 2012/0230031 A1 | 9/2012 | Hayes et al. |
| 2013/0070427 A1 | 3/2013 | Tzu |
| 2015/0313003 A1 | 10/2015 | Kasar |
| 2016/0041637 A1 | 2/2016 | Guard et al. |
| 2016/0296234 A1 | 10/2016 | Richard et al. |
| 2016/0310134 A1 | 10/2016 | Contini et al. |
| 2018/0242970 A1 | 8/2018 | Mozdzierz |
| 2018/0338383 A1 | 11/2018 | Sgroi, Jr. et al. |

FOREIGN PATENT DOCUMENTS

| | | | |
|---|---|---|---|
| DE | 102013204018 A1 * | 9/2014 | ............... H05K 5/02 |
| FR | 2920916 A1 | 3/2009 | |
| WO | 2009021827 A2 | 2/2009 | |

OTHER PUBLICATIONS

Extended European Search Report corresponding to counterpart Patent Appln. EP 18 17 3035.9 dated Oct. 15, 2018.
Chinese First Office Action dated Jul. 22, 2020 corresponding to counterpart Patent Application CN 201810462530.6.
Extended European Search Report dated Jun. 23, 2020 corresponding to counterpart Patent Application EP 20156211.3.

* cited by examiner

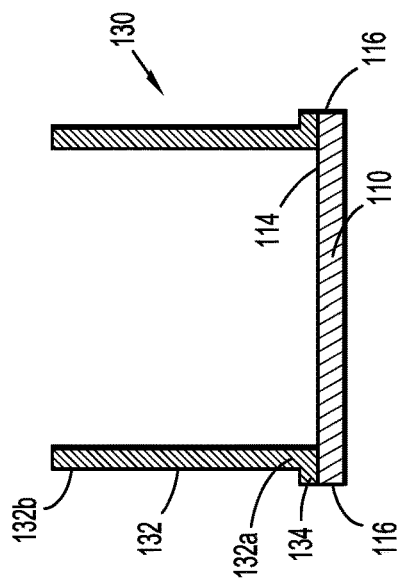
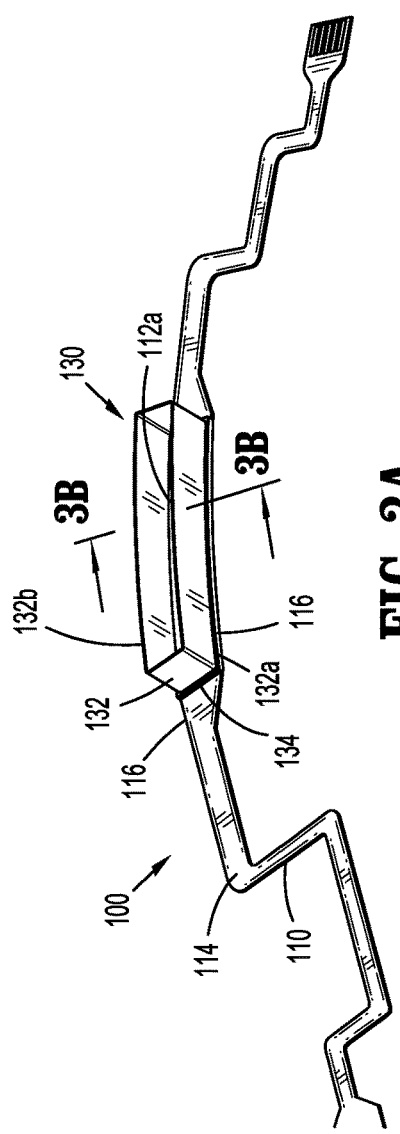
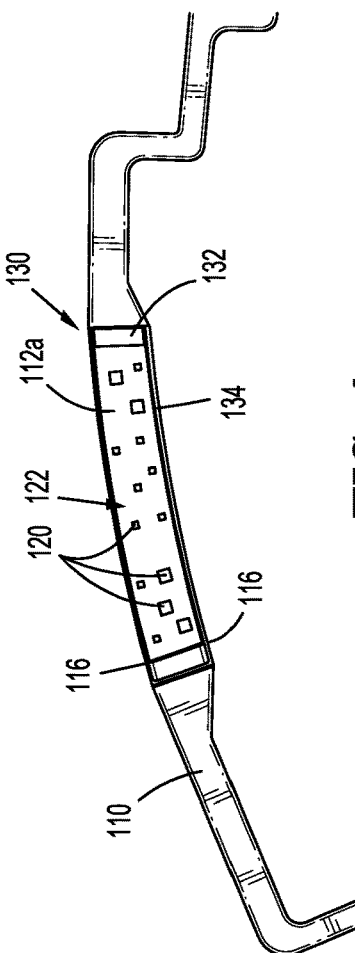

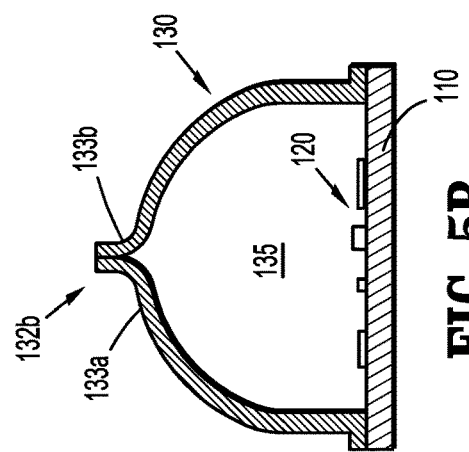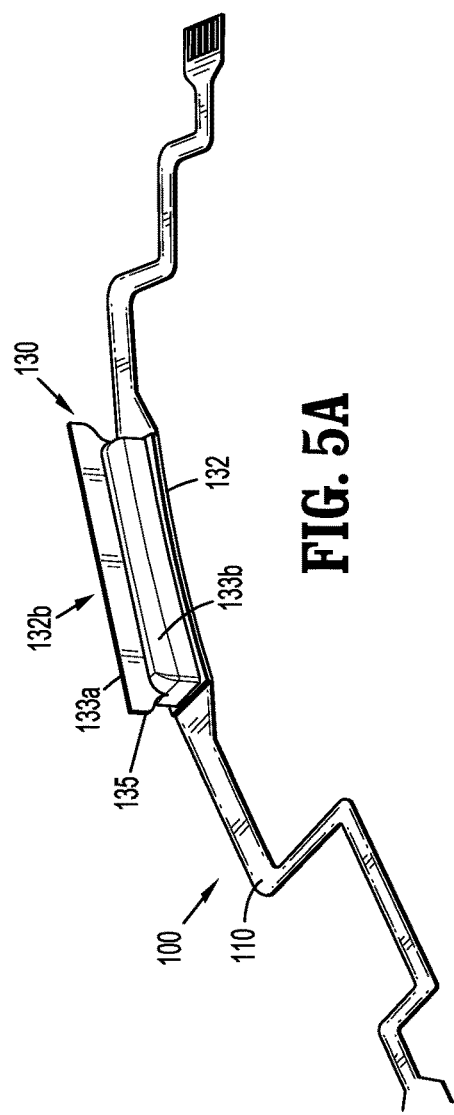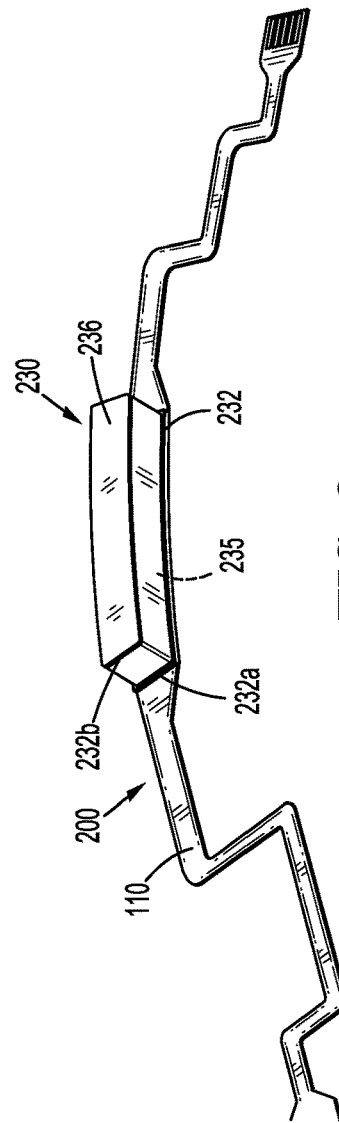

HERMETICALLY SEALED PRINTED CIRCUIT BOARDS

CROSS-REFERENCE TO RELATED APPLICATIONS

This application is a continuation-in-part of U.S. patent application Ser. No. 16/270,721, filed Feb. 8, 2019, which is a continuation-in-part application claiming the benefit of and priority to U.S. patent application Ser. No. 15/947,314, filed Apr. 6, 2018, which claims the benefit of and priority to U.S. Provisional Patent Application No. 62/508,101, filed May 18, 2017, the entire disclosures of which are incorporated by reference herein.

TECHNICAL FIELD

The present disclosure relates generally to reusable surgical devices. More particularly, the present disclosure relates to powered surgical devices with enhanced durability and increased moisture resistance.

BACKGROUND

Powered surgical devices include electronic components, such as printed circuit boards, switches, sensors, etc., to enhance the control of functions of the surgical devices. The intelligence of such surgical devices result in a higher product cost compared to currently available disposable units. Accordingly, it would be beneficial if such intelligent devices are reusable.

Reusable surgical devices must be cleaned and sterilized prior to subsequent uses. Cleaning and sterilization procedures, however, are aggressive in nature. Cleaning (e.g., washing and/or disinfecting) utilizes alkaline solutions having high pH values (e.g., a pH of 11). Autoclaving (a common method of sterilization) utilizes high pressure superheated steam (e.g., 30 PSI @ 160° C. for 20 minutes). Such environments are known to damage various electronic components. For example, surgical devices may suffer from moisture ingress during cleaning and/or sterilizing procedures which, in turn, may corrode and/or degrade the electronic components.

The electronic components of reusable surgical devices may be protected from high temperatures, steam, and/or moisture by utilizing, for example, conformal coatings, potting, sealed enclosures, and/or overmolding. The electronic components, however, may still suffer from moisture ingress during cleaning and/or sterilizing procedures (e.g., cracking or delamination of conformal coatings), and/or may be damaged during application of the protective materials (e.g., heat damage during sealing of enclosures).

Thus, it would be beneficial if the durability of the electronic components is enhanced to improve the reliability of the electronic components and/or extend the effective cycle life of the surgical devices.

SUMMARY

The surgical devices of the present disclosure include a printed circuit board having electronic components housed within a hermetically sealed chamber. The electronic components are thus protected and configured to withstand environmental stresses associated with high pH cleaning and sterilization (e.g., autowashing and/or autoclaving), thereby rendering the electronic components more durable for re-use. Additionally, methods of the present disclosure include integrating and hermetically sealing the electronic components of the printed circuit board to minimize and/or prevent damage which may occur to the electronic components during the assembly process.

In one aspect of the present disclosure, a method of assembling a hermetically sealed printed circuit board includes: securing a first end portion of a wall of a cap to a substrate around an electrical contact region of the substrate, the wall including a second end portion disposed in an open configuration; mounting an electronic component to the electrical contact region of the substrate; and sealing the second end portion of the wall closed to form a hermetically sealed chamber between the substrate and the cap to encase the electronic component therein.

In embodiments, securing the wall of the cap includes bonding the first end portion of the wall to the substrate. In some embodiments, the first end portion of the wall includes a flange and bonding the first end portion includes welding the flange to the substrate.

The substrate may be a flex cable, and mounting the electronic component may include forming a printed circuit board on the flex cable.

In embodiments, sealing the second end portion of the wall includes heat sealing sections of the wall together. In some embodiments, sealing the second end portion of the wall includes securing a cover of a cap to the wall.

Mounting the electronic component may include positioning the electronic component of the substrate a spaced distance from outer edges of the substrate, and securing the first end portion of the wall of the cap to the substrate may include bonding the first end portion to the outer edges of the substrate. Mounting of the electronic component may be performed prior or subsequent to securing the first end portion of the wall of the cap to the substrate.

In embodiments, the method further includes placing the substrate in an inert gas environment prior to mounting the electronic component and sealing the second end portion of the wall. In some embodiments, the method further includes applying a coating over the electronic component prior to sealing the second end portion of the wall.

In another aspect of the present disclosure, a method of assembling a flex cable and integrating the flex cable into a surgical device includes: assembling electronic components on a first side of a substrate of a flex cable within a perimeter of a wall secured to the substrate, the wall extending transversely from the first side of the substrate and terminating at an open end; and closing the open end of the wall such that the electronic components are disposed within a sealed chamber.

Assembling the electronic components may include forming a printed circuit board on the flex cable. The method may include placing the flex cable in an insert gas environment prior to assembling the electronic components and closing the open end of the wall, and/or applying a conformal coating over the electronic components prior to closing the open end of the wall.

The method may include placing the flex cable into an adapter assembly of the surgical device. In embodiments, the method further includes electrically connecting the flex cable to a sensor disposed within the adapter assembly. In some embodiments, the method further includes electrically connecting the flex cable with a handle assembly and an end effector of the surgical device to enable communication between the handle assembly, the adapter assembly, and the end effector.

According to a further aspect of the present disclosure, a hermetic electronic assembly includes a printed circuit board and a cap. The printed circuit board includes a plurality of electronic components disposed on a first side thereof and offset a distance from outer edges of the printed circuit board. The cap includes a wall having a first end portion and a second end portion. The first end portion is bonded to the printed circuit board entirely around the plurality of electronic components and the second end portion is heat sealed closed a distance spaced from the plurality of electronic components. The bonding of the first end portion to the printed circuit board and the heat sealing of the second portion of the wall together form a hermetic seal encasing the plurality of electronic components therein.

In embodiments, the first end portion of the cap includes a flange, and the flange is bonded to the outer edges of the printed circuit board. The printed circuit board may be a flex cable.

In another aspect of the present disclosure, a method of assembling a hermetically sealed printed circuit board includes: securing a flange of a cap against an electrical contact region on a first side of a substrate, the flange extending across a first end portion of a wall of the cap, the wall extending around the electrical contact region and including a second end portion disposed in an open configuration; and closing the second end portion of the wall to form a hermetically sealed chamber around the electrical contact region.

The method may further include mounting one or more electronic components to the electrical contact region of the substrate. Securing the flange may include aligning one or more openings defined through the flange with the one or more electronic components such that the one or more electronic components extend through the one or more openings.

Securing the flange may include bonding the flange to the substrate. Bonding the flange may include welding the flange to the substrate. Welding the flange may include welding an outer perimeter of the flange to the substrate. Bonding the flange may further include adhering a first side of the flange to the first side of the substrate.

The substrate may be a flex cable, and mounting the one or more electronic components may include forming a printed circuit board on the flex cable.

Closing the second end portion of the wall may include securing a cover of the cap to the wall. Securing the cover may include welding the cover to the wall. In other methods, closing the second end portion of the wall may include heat sealing sections of the wall together.

In yet another aspect of the present disclosure a method of hermetically sealing a printed circuit board and integrating the printed circuit board into a surgical device includes: assembling one or more electronic components onto an electrical contact region on a first side of a substrate; securing a flange of a cap against the electrical contact region, the flange extending across a first end portion of a wall of the cap, the wall extending around the electrical contact region and including a second end portion disposed in an open configuration; and closing the second end portion of the wall to form a hermetically sealed chamber around the electrical contact region.

Assembling the one or more electronic components may include forming a printed circuit board on a flex cable. The method may further include placing the flex cable into the surgical device, electrically connecting the flex cable to a sensor disposed within an adapter assembly of the surgical device; and/or electrically connecting the flex cable with a handle assembly and an end effector of the surgical device to enable communication between the handle assembly, the adapter assembly, and the end effector.

In another aspect of the present disclosure, a hermetically sealed printed circuit board assembly includes a printed circuit board and a cap. The printed circuit board includes one or more electronic components disposed on a first side thereof. The cap includes a wall having a first end portion and a second end portion. The first end portion includes a flange defining one or more openings therein corresponding to the one or more electronic components of the printed circuit board. The flange is bonded to the printed circuit board such that the one or more electronic components extend through the one or more openings of the flange. The wall extends from the flange and forms a continuous perimeter around the one or more electronic components. The second end portion of the wall is sealed to form a hermetic chamber around the one or more electronic components.

The flange may extend inwardly of the wall and across the first end portion of the wall. The cap may include a cover bonded to the second end portion of the wall. The printed circuit board may be a flex cable.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 3A is a perspective view of a flex cable of the wiring harness of FIG. 2, illustrating assembly of a cap, in an open configuration, on a substrate of the flex cable in accordance with an embodiment of the present disclosure;

FIG. 3B is a cross-sectional view of the flex cable of FIG. 3A, taken along line 3B-3B of FIG. 3A;

FIG. 4 is a top view of the flex cable of FIGS. 3A and 3B, illustrating assembly of electronic components on the substrate of the flex cable;

FIG. 5A is a perspective view of the flex cable of FIGS. 3A-4, illustrating closing of the cap towards a closed configuration;

FIG. 5B is a cross-sectional view of the flex cable of FIGS. 3A-5A, illustrating sealing of the cap to the closed configuration;

FIG. 6 is a perspective view of a flex cable in accordance with another embodiment of the present disclosure;

DETAILED DESCRIPTION

Figure 1:
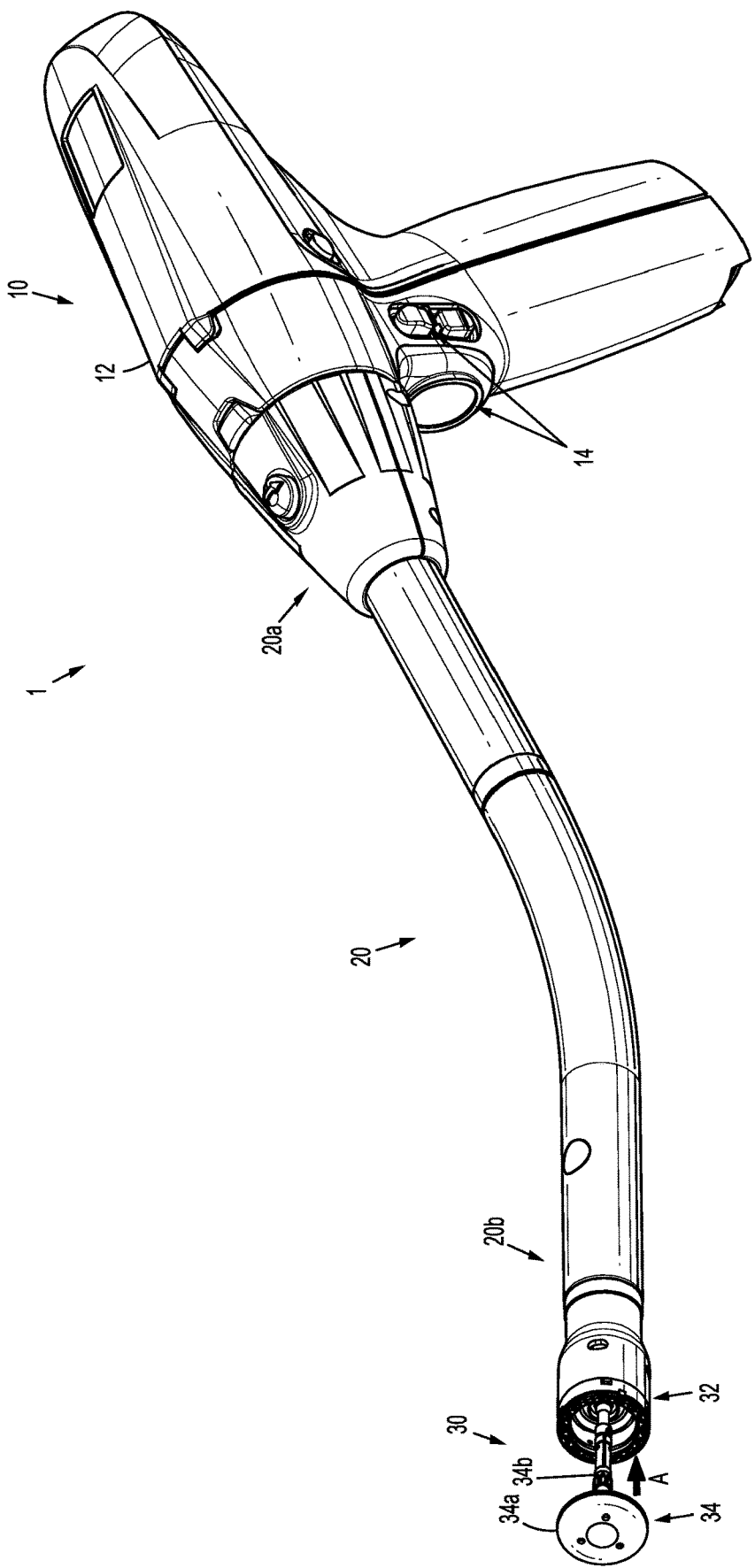
FIG. 1 is a perspective view of a surgical device in accordance with an embodiment of the present disclosure.

Surgical devices in accordance with embodiments of the present disclosure include a printed circuit board having electronic components disposed within a hermetically sealed chamber to protect the electronic components from exposure to moisture during, for example, cleaning and/or sterilizing procedures where the surgical devices may be subjected to high temperatures, steam, chemicals, and/or moisture. The electronic components of the surgical devices of the present disclosure are protected to prevent and/or resist breakdown over multiple/repeated cleaning and sterilizing cycles.

While the present disclosure is directed to printed circuit boards integrated on a flexible or flex cable of a surgical device, it is envisioned that the principles of the present disclosure are equally applicable to a range of printed circuit boards (e.g., rigid printed circuit boards, such as FR4 circuit boards) and electronic components (e.g., sensors) housed within reusable surgical devices.

Embodiments of the present disclosure are now described in detail with reference to the drawings in which like reference numerals designate identical or corresponding elements in each of the several views. Throughout this description, the term "proximal" refers to a portion of a device, or component thereof, that is closer to a user, and the term "distal" refers to a portion of the device, or component thereof, that is farther from the user.

Turning now to FIG. 1, a surgical device 1 in accordance with an embodiment of the present disclosure is shown. The surgical device 1 is in the form of a powered handheld electromechanical surgical instrument, and includes a powered handle assembly 10, an adapter assembly 20, and a tool assembly or end effector 30. The powered handle assembly 10 is configured for selective connection with the adapter assembly 20 and, in turn, the adapter assembly 20 is configured for selective connection with the end effector 30.

The surgical device 1 will only further be described to the extent necessary to disclose aspects of the present disclosure. For a detailed description of the structure and function of exemplary surgical devices, reference may be made to commonly owned U.S. Patent Publication Nos. 2016/0296234, ("the '234 Publication"), and 2016/0310134 ("the '134 Publication"), the entire contents of each of which are incorporated herein by reference.

With continued reference to FIG. 1, the handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. The adapter assembly 20 includes a proximal portion 20a configured for operable connection to the handle assembly 10 and a distal portion 20b configured for operable connection to the end effector 30. The end effector 30 including a loading unit 32 having a plurality of staples (not shown) disposed therein and an anvil assembly 34 including an anvil head 34a and an anvil rod 34b.

For a detailed description of exemplary handle assemblies, adapter assemblies, and end effectors which may be utilized in a surgical device of the present disclosure, reference may be made to the '234 and '134 Publications, the entire contents of each of which were previously incorporated herein by reference.

Figure 2:
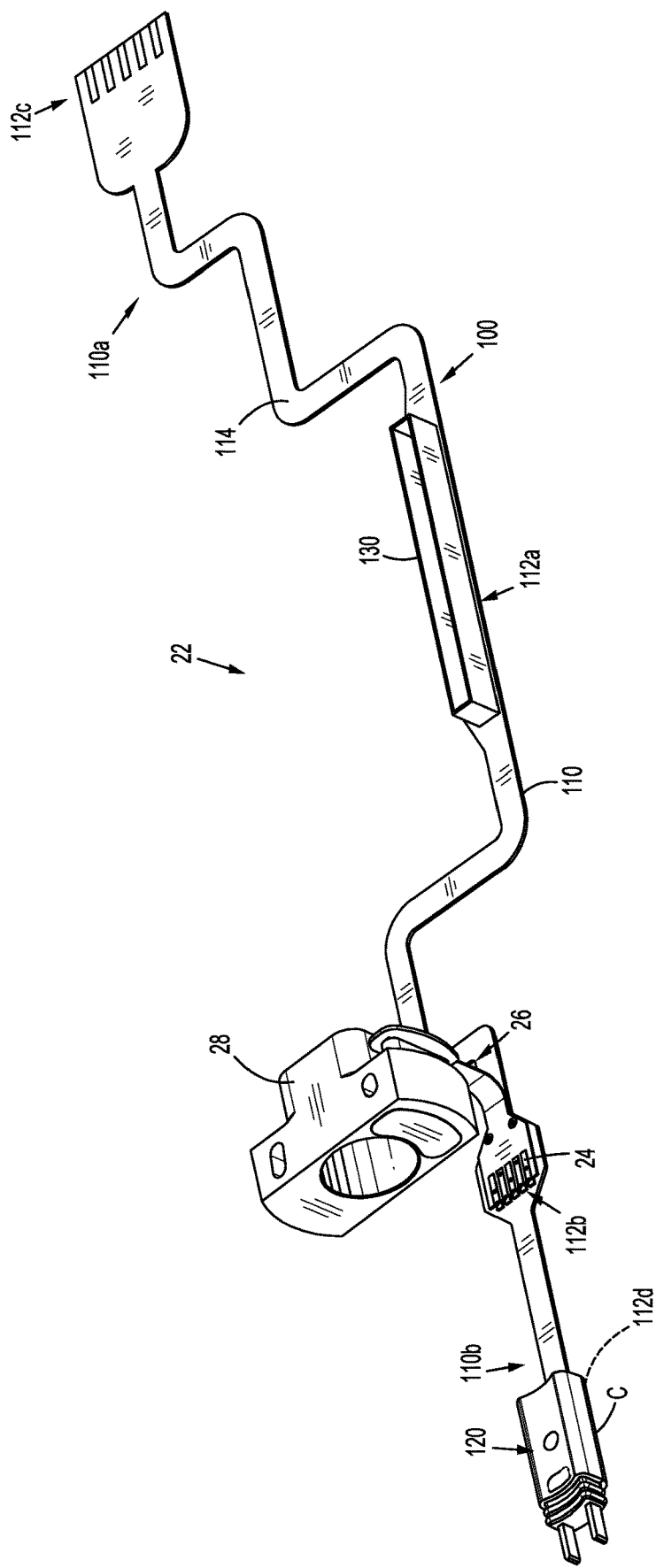
FIG. 2 is a perspective view of a wiring harness of an adapter assembly of the surgical device of FIG. 1.
Figure 7A:
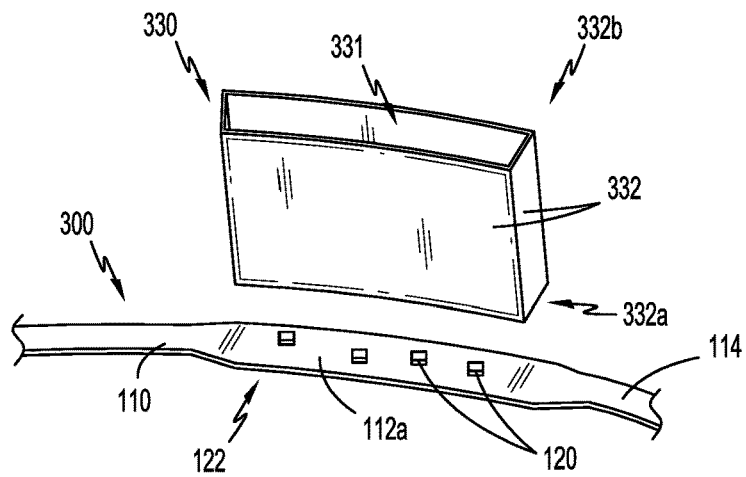
FIG. 7A is a top, perspective view of a flex cable and a cap, in an open configuration, in accordance with yet another aspect of the present disclosure.
Figure 7B:
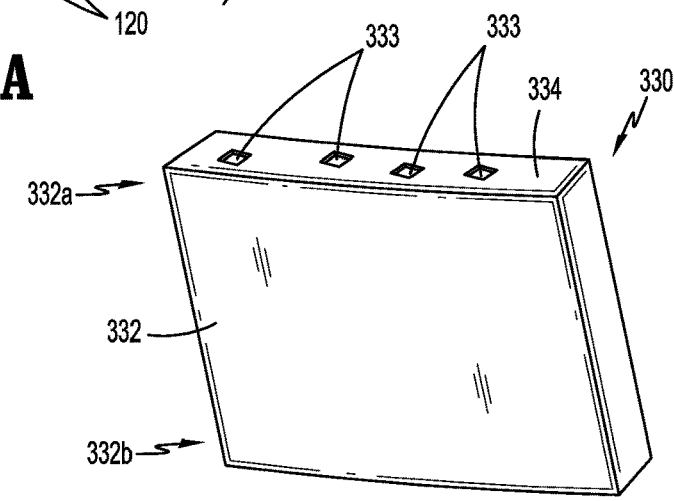
FIG. 7B is a bottom, perspective view of the cap of FIG. 7A.

With reference now to FIG. 2, in conjunction with FIG. 1, the adapter assembly 20 includes a wiring harness 22 having at least one flex cable 100 electronically interconnecting the handle assembly 10 and the end effector 30 of the surgical device 1. The wiring harness 22 of the adapter assembly 20 is configured to enable communication between the handle assembly 10 and the end effector 30, and to relay power from the handle assembly 10 to the end effector 30. For example, this communication allows for calibration and communication of data and control signals between the end effector 30 and the adapter assembly 20, as well as between the adapter assembly 20 and the handle assembly 10, thereby transferring data pertaining to the end effector 30 to the handle assembly 10 and signals from the handle assembly 10 to the end effector 30.

The flex cable 100 includes a body or substrate 110 suitable for supporting and/or electrically connecting electronic components 120 thereto. The substrate 110 is formed from one or more layers or sheets of dielectric material, such as a polymer or a ceramic, and one or more layers of conductive material, such as copper foil, that form conductive traces (not explicitly shown) in the substrate 110.

In embodiments, the substrate 110 of the flex cable 100 is formed from copper-clade polyimides, such as PYRA-LUX® or NIKAFLEX®, which are registered trademarks owned by DuPont. In some embodiments, the substrate 110 is formed from high temperature materials, such as PYRA-LUX® HT, also a registered trademark owned by DuPont. It should be understood that the substrate 110 is configured to allow for the fabrication of single or double sided flex circuits, multilayer flex circuits, and rigid flex circuits. The layers of the substrate 110 may be joined to one another by, for example, laminating, welding, and/or using adhesives, among other methods and materials within the purview of those skilled in the art.

A plurality of electrical contact regions 112 (referred to herein as first, second, third, and fourth electrical contact regions 112a-d) are disposed at terminal ends of the conductive traces (not shown) defined through the substrate 110 on a first side 114 of the flex cable 100. Each of the plurality of electrical contact regions 112 includes one or more pads (e.g., solder pads) to which electronic components 120 are joined (e.g., soldered). The electronic components 120 may be, for example, surface mount technology and/or through-hole technology, including, for example, integrated circuits (e.g., microchips, microcontrollers, microprocessors), resistors, amplifiers, inductors, capacitors, sensing elements (e.g., optical sensors, pressure sensors, capacitive sensors), buttons, switches, circuit boards, electrical connectors, cables, and/or wires, among other elements or circuitry within the purview of those skilled in the art.

The first electrical contact regions 112a includes electronic components 120 (see e.g., FIG. 4) disposed thereon. A cap 130 is disposed over the first electrical contact region 112a to hermetically seal the electronic components 120 therein, as described in further detail below. The second electrical contact region 112b is in the form of solder pads which are aligned and soldered to solder pads 24 of an adapter flex cable 26 which, in turn, is electrically coupled to a force sensor 28 disposed within the adapter assembly 20 (FIG. 1) for measuring forces of the end effector 30 (e.g., as shown in FIG. 1, the pressure applied by the anvil head 34a in the direction of arrow "A" against the distal portion 20b of the adapter assembly 20, the pressure applied by tissue acting on the anvil head 34a in a direction opposite of arrow "A" as the anvil head 34a is closed onto tissue, etc.).

With continued reference to FIG. 2, a proximal portion 110a of the substrate 110 includes the third electrical contact region 112c configured for electrical connection with the handle assembly 10 (FIG. 1). A distal portion 110b of the substrate 110 includes the fourth electrical contact region 112d (shown in phantom) coupled to an electronic component 120 in the form of an electrical connector "C" for electrical connection with the end effector 30 (FIG. 1).

It should be understood that while the flex cable 100 is shown including four electrical contact regions 112, the flex cable 100 may have any number of electrical contact regions depending upon the desired configuration and functionality of the flex cable 100, as is within the purview of those skilled in the art.

Referring now to FIGS. 3A-5B, a method of integrating and hermetically sealing a printed circuit board 122 to the substrate 110 of the flex cable 100 in accordance with an embodiment of the present disclosure is shown. As shown initially in FIGS. 3A and 3B, a cap 130, in an initial open-ended configuration, is joined to the substrate 110 of the flex cable 100 such that a wall 132 of the cap 130 extends transversely from the first side 114 of the substrate 110 and defines a closed perimeter around the first electrical contact region 112a of the substrate 110. The wall 132 may be sized to be complementary in shape with the first electrical contact region 112a of the substrate 110. The wall 132 may be formed from the same material or a different material from that of the substrate 110 (e.g., the same or a different polymeric material).

A first end portion 132a of the wall 132 includes a flange 134 that provides a flat surface or increased surface area for bonding of the wall 132 to the substrate 110. The first end portion 132a of the wall 132 may be secured to the substrate 110 by, for example, laminating or welding the flange 134 around an entire perimeter thereof to the substrate 110 to seal and form a leak-proof barrier at the junction of the substrate 110 and the cap 130. The flange 134 is positioned adjacent to and is aligned with outer edges 116 of the substrate 110, and extends along the outer edges 116 as well as across the substrate 110. A second end portion 132b of the wall 132 is open to provide access to the first electrical contact region 112a of the substrate 110. Accordingly, the cap 130 is open-ended during the initial stages of assembling the flex cable 100.

As shown in FIG. 4, electronic components 120 are assembled onto the substrate 110 at the first electrical contract region 112a disposed within the wall 132 of the cap 130 to form a printed circuit board 122. The electronic components 120 are disposed on the substrate 110 in spaced relation relative to the wall 132 of the cap 130 such that the electronic components 120 are offset a distance from the outer edge 116 of the substrate 110 to which the flange 134 of the cap 130 is bonded, as well as the portions of the flange 134 extending across the substrate 110. Placement of the electronic components 120 onto the substrate 110 in spaced relation relative to the flange 134 of the cap 130 and/or placement of the electronic components 120 onto the substrate 110 after securing the wall 132 to the substrate 110 prevents damage to the electronic components 120 that may have occurred due to heat transfer during bonding of the flange 134 to the substrate 110.

Bonding processes may require high temperatures and/or high pressure which may transfer to the substrate 110. For example, in embodiments in which the substrate 110 and the wall 132 are formed from high temperature materials, high temperatures and/or long bonding times may be required to secure the wall 132 to the substrate 110. Accordingly, assembling the electronic components 120 onto the substrate 110 a spaced distance from the flange 134 of the cap 130 either prior to or after securing the wall 132 to the substrate 110 minimizes potential damage to the electronic components 120. Further, assembling the electronic components 120 onto the substrate 110 after securing the wall 132 to the substrate 110 mitigates potential damage to the electronic components 120.

As shown in FIGS. 5A and 5B, after the electronic components 120 are assembled onto the substrate 110 of the flex cable 100, the cap 130 is sealed to a closed configuration by joining together the second end portion 132b of the wall 132. The second end portion 132b of the wall 132 is gathered and secured together in a fluid tight manner to define a hermetically sealed chamber 135 housing the electronic components 120 therein. As specifically shown in FIG. 5A, for example, the second end portion 132b of first and second sections 133a, 133b of the wall 132 are moved from an open position (see e.g., first section 133a) to a closed position (see e.g., second section 133b) so that, as shown in FIG. 5B, the second end portion 132b of the first and second sections 133a, 133b can be secured together along the entire length of the junction thereof. The second end portion 132b of the wall 132 may be secured together by, for example, laminating or welding the second end portion 132b of the wall 132 together to seal and form a leak-proof barrier at the second end portion 132 of the wall 132. Accordingly, the cap 130 is close-ended at the end stages of assembling the flex cable 100.

The space provided by the wall 132 around the electronic components 120 minimizes damage which may occur during the process of closing the second end portion 132b of the wall 132 (e.g., by spacing the second end portion 132 of the wall 132 a distance from the electronic components 120 so that heat from the bonding process does not reach the electronic components 120). The height of the wall 132 may vary depending, for example, on the space and/or distance needed to optimize protection of the electronic components 120 from the settings (e.g., heat) of the bonding process utilized. The second end portion 132b of the wall 132 may be shaped (e.g., have a domed shape) to provide additional space within the cap 130 for the electronic components 120.

While the wall 132 is shown as a single piece that is secured to the substrate 110 and to itself at the second end portion 132b thereof to form the hermetically sealed chamber 135, other configurations of the cap 130 are envisioned. For example, as shown in FIG. 6, a flex cable 200 includes a substrate 110, electronic components 120 (see e.g., FIG. 4) assembled onto the substrate 110, and a cap 230 including a wall 232 secured to the substrate 110 at a first end portion 232a thereof around the electronic components 120, and a cover 236 positioned over and secured to a second end portion 232b of the wall 232 in a fluid tight manner to define a hermetically sealed chamber 235 (shown in phantom) housing the electronic components 120 (see e.g., FIG. 4) therein. The cover 236 may be secured to the wall 232 by, for example, laminating or welding the entire outer perimeter of the cover 236 to the second end portion 232b of the wall 232 to seal and form a leak-proof barrier between the wall 232 and the cover 236. The cover 236 may be formed from the same material or a different material from that of the wall 232.

Turning now to FIGS. 7A-9B, a method of integrating and hermetically sealing a printed circuit board 122 to a substrate 110 of a flex cable 300 in accordance with another aspect of the present disclosure is shown. As shown initially in FIGS. 7A and 7B, the flex cable 300 includes electronic components 120 assembled (e.g., soldered) onto a first electrical contact region 112a on a first side 114 of the substrate 110. A cap 330, shown in an initial open configuration, is configured and dimensioned for bonding to the first electrical contact region 112a of the substrate 110. The cap 330 includes a wall 332 having first and second end portions 332a, 332b, and defines a void 331 therein. A flange 334 is disposed at the first end portion 332a of the wall 332 and includes openings 333 defined therethrough. The flange 334 extends inwardly of the wall 332 and across the first end portion 332a such that the first end portion 332a is closed by the flange 334. The second end portion 332b of the wall 332 is open.

Figure 8A:
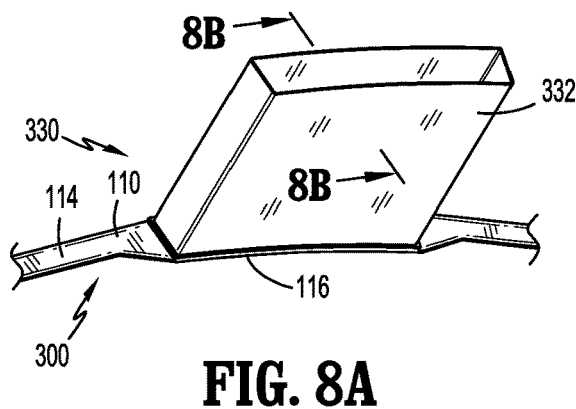
FIG. 8A is a top, perspective view of the flex cable and the cap of FIG. 7A, illustrating assembly of the cap onto a substrate of the flex cable in accordance with an aspect of the present disclosure.
Figure 8B:
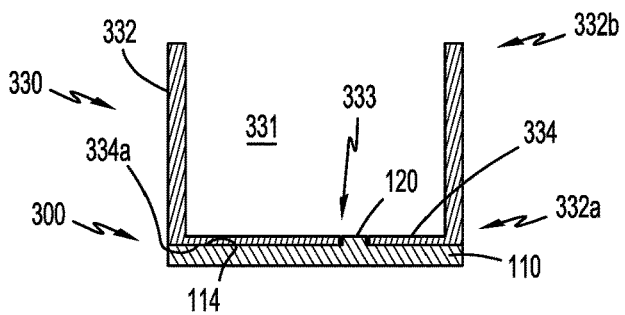
FIG. 8B is a cross-sectional view of the flex cable of FIG. 8A, taken along section line 8B-8B of FIG. 8A.
Figure 8C:
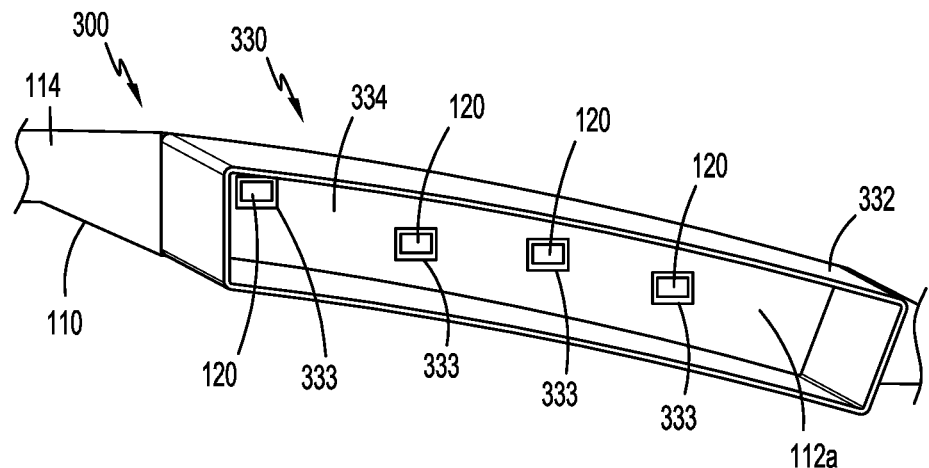
FIG. 8C is a top, perspective view of the flex cable of FIGS. 8A and 8B.

As shown in FIGS. 8A-8C, the cap 330 is joined to the substrate 110 of the flex cable 300 by positioning the flange 334 directly against the first electrical contact region 112a on the first side 114 of the substrate 110 such that the wall 332 of the cap 330 extends transversely from the first side 114 of the substrate 110 and defines a closed (e.g., continuous) perimeter around the first electrical contact region 112a of the substrate 110. The wall 332 and/or flange 334 may be sized to be complementary in shape with the first electrical contact region 112a of the substrate 110. The wall 332 and/or the flange 334 may be formed from the same material or a different material from that of the substrate 110 (e.g., the same or a different polymeric material).

The cap 330 is bonded to the substrate 110 at the flange 334. The flange 334 closes the first end portion 332a of the wall 332, except for the openings 333 extending through the flange 334. The openings 333 are sized and positioned to correspond with the electronic components 120 disposed on the substrate 110 such that the electronic components 120 are in communication with the void 331 defined within the wall 332 of the cap 330 when the flange 334 is bonded to the substrate 110. A first side 334a of the flange 334 is positioned adjacent to the first side 114 of the flex cable 300 with the openings 333 aligned with the electronic components 120 of the printed circuit board 122. The flange 334 is also aligned with outer edges 116 of the substrate 110, and extends along the outer edges 116 as well as across the substrate 110 (e.g., the flange 334 is coterminous with the first electrical contact region 112a of the substrate 110). The flange 334 provides a flat surface or increased surface area for bonding of the cap 330 to the substrate 110. The first side 334a of the flange 334 may be secured to the first side 114 of the substrate 110 by, for example, adhering, laminating, or otherwise bonding the flange 334 to the substrate 110, and/or welding the flange 334 around an entire outer perimeter thereof to the substrate 110 to seal and form a leak-proof barrier at the junction of the substrate 110 and the cap 330.

The second end portion 332b of the wall 332 is open to provide access to the electronic components 120 on the substrate 110 and to allow for bonding of the flange 334 to the substrate 110. Accordingly, the cap 330 is open-ended during the initial stages of assembling the flex cable 300. The electronic components 120 may be assembled onto the substrate 110 at the first electrical contact region 112a to form the printed circuit board 122 prior to or after the flange 334 of the cap 330 is secured to the substrate 110.

Figure 9A:
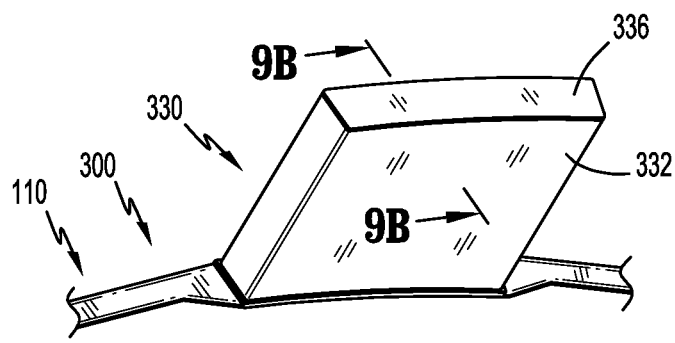
FIG. 9A is a top, perspective view of the flex cable of FIGS. 8A-8C, illustrating sealing of the cap to a closed configuration.
Figure 9B:
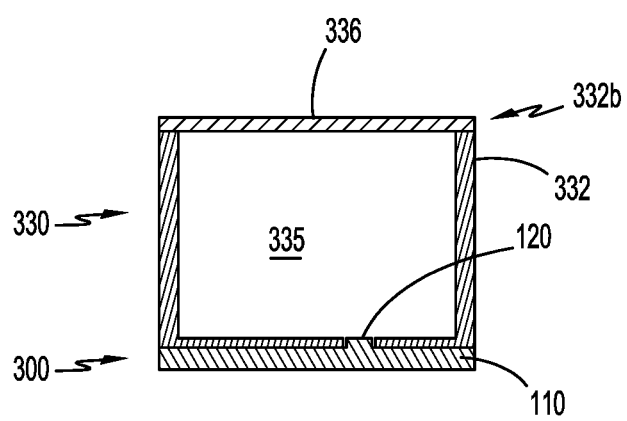
FIG. 9B is a cross-sectional view of the flex cable of FIG. 9A, taken along section line 9B-9B of FIG. 9A.

As shown in FIGS. 9A and 9B, after the electronic components 120 are assembled onto the substrate 110 of the flex cable 300 and the cap 330 is bonded to the substrate 110, the cap 330 is sealed to a closed configuration by closing the second end portion 332b of the wall 332. The cap 330 is sealed by positioning and securing a cover 336 to the second end portion 332b of the wall 332 in a fluid tight manner to define a hermetically sealed chamber 335 housing the electronic components 120 (see e.g., FIG. 8C) therein. The cover 336 may be secured to the wall 332 by, for example, laminating or welding the entire outer perimeter of the cover 336 to the second end portion 332b of the wall 332 to seal and form a leak-proof barrier between the wall 332 and the cover 336. The cover 336 may be formed from the same material or a different material from that of the wall 332. Alternatively, the second end portion 332b of the wall 332 may be gathered and secured together in a flight tight manner to define the hermetically sealed chamber 335 as described and shown above with regard to the cap 130 of FIGS. 5A and 5B.

Assembly of the flex cable 100, 200, 300 may be performed using vacuum or in the presence of an inert gas (i.e., argon, nitrogen, etc.), as is within the purview of those skilled in the art. In embodiments, the electronic components 120 are assembled onto the substrate 110 and sealed with the cap 130, 230, 330 by fully drying, assembling, and sealing the electronic components 120 in an inert gas environment, such as an inert glove box (e.g., a nitrogen-filled atmosphere), to ensure zero moisture content within the electronic components 120 and the hermetically sealed chamber 135, 235, 335.

In embodiments, a coating may be disposed over the electronic components 120 prior to sealing with the cap 130, 230, 330. The coating may be a conformal coating that protects the electronic components 120 against moisture and/or heat. Accordingly, the coating may act as an additional layer of protection from any heat that may be produced while sealing the cap 130, 230, 330 and/or in the event that the seal should fail and moisture should permeate or ingress through the cap 130, 230, 330 the coating may provide a layer of protection from the moisture that may otherwise attack the substrate 110 and/or electronic components 120.

In an embodiment, it is further contemplated that a moisture collection agent, e.g., a desiccant, may be provided within the void of the cap 130, 230, 330 prior to the sealing of the cap 130, 230, 330 to the closed configuration. For a detailed description of moisture collection agents, for use in flex circuits and the like, reference may be made to U.S. Provisional Patent Application Ser. No. 62/464,584, filed on Feb. 28, 2017, now U.S. Patent Appl. Pub. No. 2018/0242970, the entire content of which is incorporated herein by reference.

It should be understood that while the flex cable is shown and described above as being disposed within an adapter assembly of the surgical device, the flex cable may be utilized in other components of the surgical device, or other surgical devices. It should also be understood that while the flex cable is described and shown disposed within a powered surgical device, the flex cable may be utilized in non-motor driven yet powered surgical devices (e.g., reusable surgical devices subject to washing and/or sterilization procedures).

Persons skilled in the art will understand that the structures specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, the flexible cables of the present disclosure may be utilized in other surgical devices, such as robotic or powered surgical devices/instruments that are subject to sterilization procedures (e.g., autoclaving and/or autowashing). Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A hermetically sealed printed circuit board assembly comprising:
    a printed circuit board including one or more electronic components disposed on a first side thereof; and
    a cap including a wall having a first end portion and a second end portion, the first end portion including a flange defining one or more openings therein corresponding to the one or more electronic components of the printed circuit board, the flange bonded to the printed circuit board such that the one or more electronic components extend through the one or more openings of the flange, the wall extending from the flange and forming a continuous perimeter around the one or more electronic components, the second end portion of the wall sealed to form a hermetic chamber around the one or more electronic components.

2. The hermetically sealed printed circuit board assembly of claim 1, wherein the flange extends inwardly of the wall and across the first end portion of the wall.

3. The hermetically sealed printed circuit board assembly of claim 1, wherein the cap includes a cover bonded to the second end portion of the wall.

4. The hermetically sealed printed circuit board assembly of claim 1, wherein the printed circuit board is a flex cable.

5. A method of assembling a hermetically sealed printed circuit board, the method comprising:
    mounting one or more electronic components to an electrical contact region of a substrate;
    aligning one or more openings defined through a flange of a cap with the one or more electronic components such that the one or more electronic components extend through the one or more openings and securing the flange of the cap against the electrical contact region on a first side of the substrate, the flange extending across a first end portion of a wall of the cap, the wall extending around the electrical contact region and including a second end portion disposed in an open configuration; and
    closing the second end portion of the wall to form a hermetically sealed chamber around the electrical contact region.

6. The method according to claim 5, wherein securing the flange includes bonding the flange to the substrate.

7. The method according to claim 6, wherein bonding the flange includes welding the flange to the substrate.

8. The method according to claim 7, wherein welding the flange includes welding an outer perimeter of the flange to the substrate.

9. The method according to claim 8, where bonding the flange further includes adhering a first side of the flange to the first side of the substrate.

10. The method according to claim 5, wherein the substrate is a flex cable, and mounting the one or more electronic components includes forming a printed circuit board on the flex cable.

11. The method according to claim 5, wherein closing the second end portion of the wall includes securing a cover of the cap to the wall.

12. The method according to claim 11, wherein securing the cover includes welding the cover to the wall.

13. The method according to claim 5, wherein closing the second end portion of the wall includes heat sealing sections of the wall together.

14. A method of hermetically sealing a printed circuit board and integrating the printed circuit board into a surgical device, the method comprising:
    assembling one or more electronic components onto an electrical contact region on a first side of a substrate;
    securing a flange of a cap against the electrical contact region of the substrate, the flange extending across a first end portion of a wall of the cap, the wall extending around the electrical contact region and including a second end portion disposed in an open configuration; and
    closing the second end portion of the wall to form a hermetically sealed chamber around the electrical contact region.

15. The method according to claim 14, wherein assembling the one or more electronic components includes forming a printed circuit board on a flex cable.

16. The method according to claim 15, further comprising placing the flex cable into the surgical device.

17. The method according to claim 16, further comprising electrically connecting the flex cable to a sensor disposed within an adapter assembly of the surgical device.

18. The method according to claim 17, further comprising electrically connecting the flex cable with a handle assembly and an end effector of the surgical device to enable communication between the handle assembly, the adapter assembly, and the end effector.

19. A method of assembling a hermetically sealed printed circuit board, the method comprising:
    securing a flange of a cap against an electrical contact region on a first side of a substrate by welding the flange to the substrate, the flange extending across a first end portion of a wall of the cap, the wall extending around the electrical contact region and including a second end portion disposed in an open configuration; and
    closing the second end portion of the wall to form a hermetically sealed chamber around the electrical contact region.

20. The method according to claim 19, wherein closing the second end portion of the wall includes welding a cover of the cap to the wall.

* * * * *